US006998399B2

(12) United States Patent
Galli et al.

(10) Patent No.: US 6,998,399 B2
(45) Date of Patent: Feb. 14, 2006

(54) 4-(1,3,4-THIADIAZOL-2-YL)-1, 4-DIAZABICYCLO-[3.2.2]NONANE DERIVATIVES, PREPARATION AND THERAPEUTIC USE THEREOF

(75) Inventors: Frédéric Galli, Vaucresson (FR); Odile Leclerc, Massy (FR); Alistair Lochead, Charenton le Pont (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 10/495,935

(22) PCT Filed: Nov. 21, 2002

(86) PCT No.: PCT/FR02/03986

§ 371 (c)(1),
(2), (4) Date: May 18, 2004

(87) PCT Pub. No.: WO03/044020

PCT Pub. Date: May 30, 2003

(65) Prior Publication Data
US 2005/0020599 A1    Jan. 27, 2005

(30) Foreign Application Priority Data
Nov. 23, 2001   (FR) .................................. 01 15154

(51) Int. Cl.
*A61P 25/00* (2006.01)
*A61K 31/55* (2006.01)
*C07D 471/08* (2006.01)

(52) U.S. Cl. ........................ 514/219; 514/221; 540/556
(58) Field of Classification Search ................ 514/219, 514/221; 540/556
See application file for complete search history.

(56) References Cited

U.S. PATENT DOCUMENTS

| | | | |
|---|---|---|---|
| 5,478,939 A | 12/1995 | Trybulski et al. | 544/336 |
| 6,407,095 B1 | 6/2002 | Lochead et al. | 514/221 |
| 2004/0029884 A1 | 2/2004 | Gallet et al. | 514/249 |

FOREIGN PATENT DOCUMENTS

| | | |
|---|---|---|
| EP | 0307140 | 3/1989 |
| WO | WO 00/34279 | 6/2000 |
| WO | WO 01/92260 | 12/2001 |

*Primary Examiner*—Brenda Coleman
(74) *Attorney, Agent, or Firm*—Balaram Gupta

(57) ABSTRACT

The invention relates to compounds of the Formula I, to pharmaceutical compositions comprising them, and to the method of use thereof in the treatment or prevention of disorders associated with a dysfunction of the nicotinic receptors.

4 Claims, No Drawings

4-(1,3,4-THIADIAZOL-2-YL)-1,4-DIAZABICYCLO-[3.2.2]NONANE DERIVATIVES, PREPARATION AND THERAPEUTIC USE THEREOF

This application is a National Stage entry under 35 U.S.C. § 371 of International application No. PCT/FR02/03986 filed Nov. 21, 2002, which is incorporated herein by reference in its entirety.

The present invention relates to compounds, which are ligands of the nicotinic receptors, these compounds being useful in the treatment or prevention of disorders associated with dysfunction of the nicotinic receptors, especially in the central nervous system.

The compounds of the present invention correspond to the general formula (I)

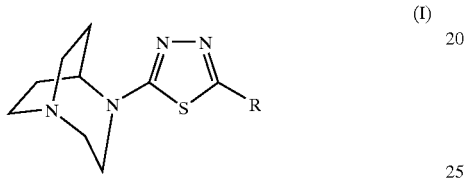

in which R represents a $(C_3-C_6)$cycloalkyl group or a phenyl group optionally substituted with one or more groups chosen from a halogen atom, a $(C_1-C_6)$alkyl, $(C_1-C_6)$alkoxy, nitro, amino, di$(C_1-C_3)$alkylamino, trifluoromethoxy, trifluoromethyl, cyano, hydroxyl or methylenedioxy group or a 1-piperidyl, 4-morpholinyl, 1-pyrrolidinyl, 1-azetidinyl, 1-azepinyl, pyridyl, thienyl, pyrazinyl, furyl, benzofuryl, benzothienyl, indolyl, pyrimidinyl, isoxazolyl, phenoxazinyl, phenoxathiinyl, dibenzofuryl, dibenzothienyl, pyrrolyl or naphthyl group, each of these groups possibly being substituted with one or more groups chosen from a halogen atom and a $(C_1-C_6)$alkyl, $(C_1-C_6)$alkoxy, trifluoromethoxy, trifluoromethyl, nitro, cyano, hydroxyl, amino, di$(C_1-C_3)$ alkylamino or $(C_3-C_8)$cycloalkylamino group.

A subgroup of preferred compounds is that of the compounds of general formula (I) in which R represents a phenyl group substituted with one or more halogen atoms or with one or more $(C_1-C_6)$alkyl, $(C_1-C_6)$alkoxy, nitro, amino, trifluoromethoxy, trifluoromethyl, cyano, hydroxyl or methylenedioxy groups, or a pyridyl group, or a thienyl group optionally substituted with a halogen atom, or a pyrazinyl group.

The compounds of the invention may exist in the form of bases or of acid-addition salts.

In accordance with the invention, the compounds of general formula (I) may be prepared according to the following scheme, by reacting 1,4-diazabicyclo[3.2.2]nonane of formula (II) with a compound of general formula (III) in which R is as defined above.

Thus, a nucleophilic substitution reaction may be performed in the presence of a strong base such as caesium carbonate or triethylamine. A Buchwald coupling reaction (J. Org. Chem., 1997, 62, 6066–6068) may also be performed, in the presence of a palladium catalyst such as palladium acetate, tris(dibenzylideneacetone)dipalladium (0), etc., a complexation ligand such as triphenylphosphine, tributylphosphine or 2,2'-bis(diphenylphosphino)-1,1'-binaphthyl, and a base, for example an organic base such as sodium t-butoxide, or a mineral base such as caesium carbonate, or any other similar coupling reaction.

Scheme

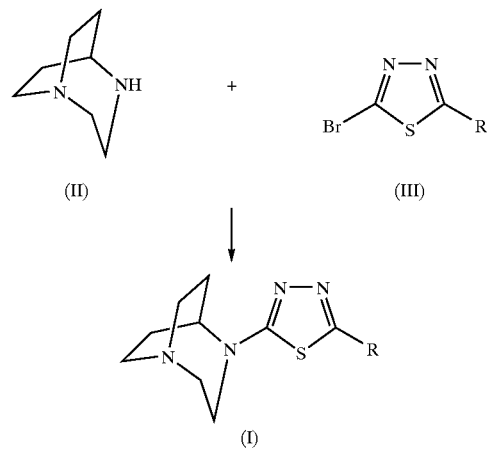

The preparation of 1,4-diazabicyclo[3.2.2]nonane is described in J. Med. Chem., 1993, 36, 2311–2320.

The compounds of general formula (III) are commercially available or are accessible via methods described in the literature, for example in J. Het. Chem., 1983, 73.

The example that follows illustrates the preparation of the compounds of the invention. The elemental microanalyses and the IR and NMR spectra, and also, in certain cases, the X-ray diffraction spectra, confirm the structures of the compounds obtained.

The number given in parentheses in the example title corresponds to that in the first column of the table given later.

In the compound names, the hyphen "-" forms part of the name, and the underscore line "" merely serves to indicate the line break; it should be deleted if it does not occur at a line break, and should not be replaced with either a normal hyphen or a space.

EXAMPLE (COMPOUND 1)

4-[(5-Phenyl)-1,3,4-thiadiazol-2-yl]-1,4-diazabicyclo [3.2.2]nonane hydrobromide 1:2

0.5 g (4 mmol) of 1,4-diazabicyclo[3.2.2]nonane, 1 g (4 mmol) of 2-bromo-5-phenyl-1,3,4-thiadiazole and 0.6 ml (4.4 mmol) of triethylamine dissolved in 15 ml of dry tetrahydrofuran are successively introduced into a 25 ml round-bottomed flask, and the mixture is refluxed for 20 hours.

The solvent is evaporated off under reduced pressure and the residue is purified by chromatography on a column of silica gel, eluting with a 93/7/0.7 mixture of chloroform, methanol and aqueous ammonia.

0.25 g of product is obtained, the dihydrobromide of which is prepared by adding a solution of 33% hydrobromic acid in acetic acid. The crystals obtained are collected by filtration.

0.21 g of dihydrobromide is obtained.

Melting point: 297–300° C.

The table that follows illustrates the chemical structures and the physical properties of a number of compounds of the invention.

In the "Salt" column, "-" denotes a compound in base form and "HBr" denotes a hydrobromide. The acid:base molar ratios are indicated adjacent.

In the "m.p. (° C.)" column, "(d)" denotes a melting point with decomposition.

TABLE

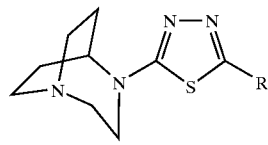

(I)

| No. | R | Salt | m.p. (° C.) |
| --- | --- | --- | --- |
| 1 | $C_6H_5$ | HBr 2:1 | 297–300 |
| 2 | 3-$CH_3$—$C_6H_4$ | HBr 2:1 | 312–313 |
| 3 | 2-F—$C_6H_4$ | HBr 2:1 | 265–267 |
| 4 | 3-$CF_3$—$C_6H_4$ | HBr 3:1 | 254 |
| 5 | 5-Br-2-thienyl | HBr 2:1 | 238–240 |
| 6 | 2-pyrazinyl | HBr 3:1 | 285–288 |
| 7 | 4-$CH_3$—$C_6H_4$ | HBr 2:1 | 274–275 |
| 8 | 4-pyridyl | HBr 3:1 | 348–350 |
| 9 | 3-$NO_2$—$C_6H_4$ | — | 174–175 |
| 10 | 3-$NH_2$—$C_6H_4$ | — | 181–182 |
| 11 | 3-$OCF_3$—$C_6H_4$ | HBr 2:1 | 248–250 |
| 12 | 3,4-$(CH_3)_2$—$C_6H_3$ | — | 129–131 |
| 13 | 3,4-$(OCH_2O)$—$C_6H_3$ | — | 162–164 |
| 14 | 3-Cl—$C_6H_4$ | HBr 2:1 | 295–300 |
| 15 | 2-$NO_2$-4-$CF_3$—$C_6H_3$ | HBr 2:1 | 211–215 |
| 16 | 3-thienyl | — | 140–143 |
| 17 | 2,6-$F_2$—$C_6H_3$ | HBr 2:1 | 276–279 |
| 18 | 4-$(CH_3)_2$N—$C_6H_4$ | — | 159–161 |
| 19 | 5-indolyl | — | 240–261 |
| 20 | 2-thienyl | HBr 1:1 | 266–268 |
| 21 | 2,4-$(OCH_3)_2$-pyrimidin-5-yl | HBr 1:1 | 250 (d) |
| 22 | 2-benzofuryl | HBr 2:1 | 289–290 |
| 23 | 1-phenoxathiinyl | HBr 2:1 | 255–256 |
| 24 | 5-$CH_3$-2-thienyl | HBr 2:1 | 256–257 |
| 25 | 4-$CH_3$-2-thienyl | HBr 2:1 | 301–302 |
| 26 | 3-pyridyl | HBr 2:1 | 311–312 |
| 27 | 3-furyl | HBr 2:1 | 285–286 |
| 28 | 3,5-$(CH_3)_2$-1,2-oxazol-4-yl | HBr 2:1 | 294–295 |
| 29 | 4-$OCH_3$-3-pyridyl | HBr 2:1 | 281–282 |
| 30 | 2-benzothienyl | — | 155–156 |
| 31 | 2-dibenzothienyl | — | 241–242 |
| 32 | 2-dibenzofuryl | HBr 2:1 | 281–282 |
| 33 | 2-pyrrolyl | HBr 2:1 | 255 (d) |
| 34 | 4-$OCH_3$—$C_6H_4$ | HBr 2:1 | 274–275 |
| 35 | 4-F—$C_6H_4$ | HBr 2:1 | 270–271 |

The compounds of the invention were studied as regards their affinity with respect to nicotinic receptors containing the $\alpha_7$ subunit, according to the methods described by Marks and Collins in *J. Pharmacol. Exp. Ther.*, 1982, 22, 564 and Marks et al. in *Mol. Pharmacol.*, 1986, 30, 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 minutes. The pellet is discarded and the supernatant is centrifuged at 8000×g for 20 minutes at 4° C. The pellet is recovered and homogenized using a Polytron™ mill in 15 volumes of double-distilled water at 4° C., followed by centrifugation at 8000×g for 20 minutes. The pellet is discarded and the supernatant and the buffy coat are centrifuged at 40 000×g for 20 minutes. The pellet is recovered, resuspended with 15 volumes of double-distilled water at 4° C. and centrifuged again at 40 000×g for 20 minutes, before storing it at −80° C.

On the day of the experiment, the tissue is thawed slowly and suspended in 5 volumes of buffer. 150 µl of this membrane suspension are preincubated at 37° C. for 30 minutes, in the dark, in the presence or absence of the test compound. Next, the membranes are incubated for 60 minutes at 37° C., in the dark, in the presence of 50 µl of 1 nM [$^3$H]α-bungarotoxin in a final volume of 250 µl of 20 mM HEPES buffer. The reaction is stopped by filtration through Whatman GF/C™ filters pretreated for 3 hours with 0.05% polyethyleneimine. The filters are rinsed with 2×5 ml of buffer at 4° C. and the radioactivity retained on each filter is measured by liquid scintigraphy. The non-specific binding in the presence of α-bungarotoxin at 1 µM final is determined; the non-specific binding represents about 60% of the total binding recovered on the filter. For each concentration of test compound, the percentage of inhibition of the specific binding of [$^3$H]α-bungarotoxin is determined, followed by calculation of the $IC_{50}$ value, which is the concentration of compound that inhibits the specific binding by 50%.

The $IC_{50}$ values for the purest compounds of the invention are between 0.001 and 0.5 µM.

The preceding results show that the compounds of the invention are ligands for the $\alpha_7$ subunits of the nicotinic receptor.

The results of the tests suggest the use of the compounds in the treatment or prevention of disorders associated with dysfunction of the nicotinic receptors, in particular on the central nervous system.

These disorders comprise cognitive impairment, more specifically memory impairment, but also attention impairment, associated with Alzheimer's disease, pathological ageing (Age Associated Memory Impairment, AAMI), Parkinson's syndrome, trisomy 21 (Down's syndrome), Korsakoff's alcoholic syndrome and vascular dementia (multi-infarct dementia, MID).

The compounds of the invention may also be useful in the treatment of the motor disorders observed in Parkinson's disease or other neurological diseases such as Huntington's chorea, Tourette's syndrome, tardive dyskinesia and hyperkinesia.

The compounds of the invention can also constitute a curative or symptomatic treatment for acute neurodegenerative pathologies such as strokes and cerebral hypoxic episodes, and also chronic neurodegenerative pathologies such as Alzheimer's disease. They can also be used in psychiatric pathologies: schizophrenia, depression, anxiety, panic attacks, compulsive and obsessive behaviour.

They can prevent the symptoms caused by withdrawal from tobacco, from alcohol and from various substances that induce dependence, such as cocaine, LSD, cannabis and benzodiazepines.

Accordingly, one subject of the present invention is also pharmaceutical compositions containing an effective dose of at least one compound according to the invention, in the form of the base or of a pharmaceutically acceptable salt or solvate, and as a mixture, where appropriate, with suitable excipients.

The said excipients are chosen according to the pharmaceutical form and the desired mode of administration.

The pharmaceutical compositions according to the invention may thus be intended for oral, sublingual, subcutaneous, intramuscular, intravenous, topical, intratracheal, intranasal, transdermal, rectal or intraocular administration.

The unit forms of administration may be, for example, tablets, gel capsules, granules, powders, oral or injectable solutions or suspensions, transdermal patches or suppositories. Ointments, lotions, and eye drops may be envisaged for topical administration.

The said unit forms are dosed to allow a daily administration of from 0.01 to 20 mg of active principle per kg of body weight, according to the presentation form.

In order to prepare tablets, a pharmaceutical vehicle which may be composed of diluents such as, for example, lactose, microcrystalline cellulose, starch and formulation adjuvants, for instance binders (polyvinylpyrrolidone, hydroxypropylmethylcellulose, etc.), glidants, for instance silica, lubricants, for instance magnesium stearate, stearic acid, glyceryl tribehenate or sodium stearylfumarate is added to the micronized or non-micronized active principle. Wetting agents or surfactants such as sodium lauryl sulphate may also be added.

The preparation techniques may be direct tabletting, dry granulation, wet granulation or hot melting.

The tablets may be plain, coated, for example with sucrose, or coated with various polymers or other suitable materials. They may be designed to allow a rapid, delayed or sustained release of the active principle by means of polymer matrices or specific polymers used in the coating.

In order to prepare gel capsules, the active principle is mixed with dry pharmaceutical vehicles (simple mixing, dry or wet granulation, or hot melting) or liquid or semi-solid pharmaceutical vehicles.

The gel capsules may be hard or soft, and uncoated or film-coated, so as to have rapid, sustained or delayed activity (for example for an enteric form).

A composition in the form of a syrup or elixir for administration in the form of drops may contain the active principle together with a sweetener, preferably a calorie-free sweetener, methylparaben or propylparaben as antiseptic, a flavour enhancer and a colorant.

The water-dispersible powders and granules may contain the active principle mixed with dispersants or wetting agents, or dispersants such as polyvinylpyrrolidone, and also with sweeteners and flavour enhancers.

For rectal administration, use is made of suppositories prepared with binders that melt at the rectal temperature, for example cocoa butter or polyethylene glycols.

For parenteral administration, aqueous suspensions, isotonic saline solutions or injectable sterile solutions containing pharmacologically compatible dispersants and/or wetting agents, for example propylene glycol or butylene glycol, are used.

The active principle may also be formulated in the form of microcapsules, optionally with one or more supports or additives, or with a polymer matrix or with a cyclodextrin (transdermal patches, sustained-release forms).

The topical compositions according to the invention comprise a medium that is compatible with the skin. They may especially be in the form of aqueous, alcoholic or aqueous-alcoholic solutions, gels, water-in-oil or oil-in-water emulsions having the appearance of a cream or a gel, microemulsions or aerosols, or alternatively in the form of vesicular dispersions containing ionic and/or nonionic lipids. These presentation forms are prepared according to the usual methods of the fields under consideration.

Finally, the pharmaceutical compositions according to the invention may contain, along with a compound of general formula (I), other active principles that may be useful in the treatment of the disorders and diseases indicated above.

The invention claimed is:

1. A compound of the formula (I)

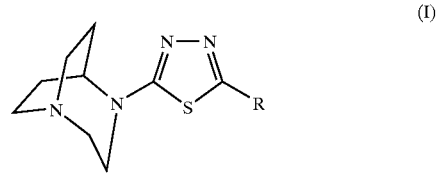

in which R represents a $(C_1-C_6)$cycloalkyl group or a phenyl group optionally substituted with one or more groups chosen from a halogen atom, a $(C_1-C_6)$alkyl, $(C_1-C_6)$alkoxy, nitro, amino, di$(C_1-C_6)$alkylamino, trifluoromethoxy, trifluoromnethyl, cyano, hydroxyl or methylenedioxy group or a 1-piperidyl, 4-morpholinyl, 1-pyrrolidinyl, 1-azetidinyl, 1-azepinyl, pyridyl, thienyl, pyrazinyl, furyl, benzofmyl, beuzothienyl, indolyl, pyrimidinyl, isoxazolyl, phenoxzinyl, phenoxathienyl, dibeuzofuryl, dibeuzothienyl, pyrrolyl or naphthyl group, each of these groups possibly being substituted with one or more groups chosen from a halogen atom and a $(C_1-C_6)$alkyl, $(C_1-C_6)$alkoxy, trifluoromethoxy, trifluoromethyl, nitro, cyano, hydroxyl, amino, di$(C_1-C_3)$alkylamino or $(C_3-C_8)$cycloalkylamino group, in base form or in the form of an acid-addition salt.

2. The compound according to claim 1 wherein R. represents a phenyl group substituted with one or more halogen atoms or with one or more $(C_1-C_6)$alkyl, $(C_1-C_6)$alkoxy, nitro, amino, trifluoromethoxy, trifluoromethyl, cyano, hydroxyl or methylenedioxy groups, or a pyridyl group, or a thienyl group optionally substituted with a halogen atom, or a pyrazinyl group.

3. A pharmaceutical composition containing a compound according to claim 1 combined with an excipient.

4. A pharmaceutical composition containing a compound according to claim 2 combined with an excipient.

* * * * *

UNITED STATES PATENT AND TRADEMARK OFFICE
CERTIFICATE OF CORRECTION

PATENT NO.        : 6,998,399 B2
APPLICATION NO. : 10/495935
DATED             : February 14, 2006
INVENTOR(S)      : Frederic Galli et al.

It is certified that error appears in the above-identified patent and that said Letters Patent is hereby corrected as shown below:

Column 1, Line 35 - 36 reads:

"benzothienyl, indolyl, pyrimidinyl, isoxazolyl, phenoxazinyl, phenoxathiinyl, dibenzofuryl, dibenzothienyl, pyrrolyl"
and should read as:

--benzothienyl, indolyl, pyrimidinyl, isoxazolyl, phenoxazinyl, phenoxathienyl, dibenzofuryl, dibenzothienyl, pyrrolyl--

Column 2, Line 38 reads:

"name, and the underscore line "" merely serves to indicate"

and should read as:

--name, and the underscore line "_" merely serves to indicate--

Column 6, Line 24 reads:

"in which R represents a $(C_1\text{-}C_6)$cycloalkyl group or a phenyl"

and should read as:

--in which R represents a $(C_3\text{-}C_6)$cycloalkyl group or phenyl--

Column 6, Lines 27-28 read:

"amino, di$(C_1\text{-}C_6)$alkylamino, trifluoromethoxy, trifluorom-nethyl, cyano, hydroxyl and methylenedioxy group or a "

and should read as:

--amino, di$(C_1\text{-}C_3)$alkylamino, trifluoromethoxy, trifluoromethyl, cyano, hydroxyl and methylenedioxy group or a--

UNITED STATES PATENT AND TRADEMARK OFFICE
CERTIFICATE OF CORRECTION

PATENT NO. : 6,998,399 B2
APPLICATION NO. : 10/495935
DATED : February 14, 2006
INVENTOR(S) : Frederic Galli et al.

It is certified that error appears in the above-identified patent and that said Letters Patent is hereby corrected as shown below:

Column 6, Line 30-33 reads:

"1-azepinyl, pyridyl, thienyl, pyrazinyl, furyl, benzofmyl, beuzothienyl, indolyl, pyrimidinyl, isoxazolyl, phenoxzinyl, phenoxathienyl, dibeuzofuryl, dibeuzothienyl, pyrrolyl or"
and should read as:

--1-azepinyl, pyridyl, thienyl, pyrazinyl, furyl, benzofuryl, benzothienyl, indolyl, pyrimidinyl, isoxazolyl, phenoxazinyl, phenoxathienyl, dibenzofuryl, dibenzothienyl, pyrrolyl or--

Column 6, Line 39 reads:

"2. The compound according to claim 1 wherein R. rep-"

and should read. as:

--2. The compound according to claim 1 wherein R rep- --

Signed and Sealed this

Twelfth Day of December, 2006

JON W. DUDAS
*Director of the United States Patent and Trademark Office*